United States Patent [19]

Boodman et al.

[11] 4,075,254

[45] Feb. 21, 1978

[54] HYDROGENATION OF ALKYLSTYRENE TO PRODUCE ALKYLBENZENE USING COPPER CHROMITE CATALYSTS

[75] Inventors: Norman S. Boodman; Jack W. Walter, both of Penn Hills Township, Allegheny County, Pa.

[73] Assignee: United States Steel Corporation, Pittsburgh, Pa.

[21] Appl. No.: 792,374

[22] Filed: Apr. 29, 1977

Related U.S. Application Data

[63] Continuation-in-part of Ser. No. 629,956, Nov. 7, 1975, abandoned.

[51] Int. Cl.$^2$ .................. B01J 23/86; C07C 15/02
[52] U.S. Cl. .................................. 260/667; 252/467; 252/476; 260/668 R
[58] Field of Search ................ 260/667, 668 R; 252/454, 458, 467, 476

[56] References Cited

U.S. PATENT DOCUMENTS

| | | | |
|---|---|---|---|
| 1,889,388 | 11/1932 | Smith | 252/467 X |
| 2,129,507 | 9/1938 | Salzberg | 252/458 X |
| 2,137,407 | 11/1938 | Lazier | 252/458 X |
| 2,623,078 | 12/1952 | Bewley et al. | 260/667 X |
| 3,205,272 | 9/1965 | Pollitzer | 260/667 X |
| 3,334,149 | 8/1967 | Akin et al. | 260/667 X |
| 3,646,235 | 2/1972 | Little et al. | 260/667 |
| 3,769,358 | 10/1973 | Neta et al. | 260/667 |
| 3,925,490 | 12/1975 | Reich et al. | 252/467 X |
| 3,935,128 | 1/1976 | Fein et al. | 252/467 |

*Primary Examiner*—Daniel E. Wyman
*Assistant Examiner*—Thomas A. Waltz
*Attorney, Agent, or Firm*—W. Gary Goodson

[57] ABSTRACT

A process for selective non-destructive catalytic hydrogenation of alkylstyrene such as α-methylstyrene in a mixed α-methylstyrene and cumene feed stream wherein the hydrogenation is conducted in the presence of a copper chromite catalyst. Preferably the hydrogenation is carried out at a pressure of between about 5 psia and about 300 psia. Use of this catalyst allows hydrogen streams containing up to about 30 per cent by volume carbon monoxide to be utilized.

14 Claims, No Drawings

4,075,254

HYDROGENATION OF ALKYLSTYRENE TO PRODUCE ALKYLBENZENE USING COPPER CHROMITE CATALYSTS

This application is a continuation-in-part of U.S. Ser. No. 629,956 filed Nov. 7, 1975, now abandoned.

BACKGROUND OF THE INVENTION

This invention relates to a hydrogenation process for selective non-destructive hydrogenation of alkylstyrene to produce alkylbenzene.

The major process employed for phenol manufacture involves hydroperoxidation of cumene (isopropyl benzene), followed by acid cleavage of the resulting hydroperoxide to produce phenol and acetone. A by-product of the hydroperoxidation reaction is $\alpha,\alpha$-dimethylbenzyl alcohol which, in turn can lose a mole of water to form $\alpha$-methylstyrene. In order to obtain improved efficiency in the phenol production process from cumene, considerable effort has been made to convert the $\alpha$-methylstyrene by-product to cumene by hydrogenation and recycling to the process. Also, in the manufacture of other alkylphenols via hydrocarbon hydroperoxidation, as for example, cresols from mixed cymenes, analogous chemical reactions take place. In this process, hydrogenation of the dimethylstyrene produces cymene.

In order to achieve economical hydrogenation of the alkylstyrene derivatives, it is desirable that the reaction occur under moderate conditions, in a manner that avoids excessive consumption of hydrogen, which can utilize relatively impure styrene feed streams and which can utilize impure hydrogen streams and especially those containing carbon monoxide. Also, it is important that the catalyst system be one which does not require expensive regeneration procedures and be one which has a relatively long catalyst life. Numerous catalyst systems have appeared in the art as the expensive platinums or palladium catalysts, such as disclosed in U.S. Pat. No. 3,127,452 and U.S. Pat. No. 3,436,429 which claim to eliminate the hydrogenation of the aromatic ring while selectively hydrogenating the alkenyl substituent on the aromatic ring. However, in practice these catalysts have been only partially successful in eliminating aromatic ring hydrogenation. Furthermore, a significant drawback relates to the fact that when attempting to use low grade hydrogen-containing streams such as those available from gasification or partial gasification of coal or oil, or with waste gases from commercial operations that contain appreciable concentrations of carbon monoxide, serious degradation and poisoning of the catalyst occurs.

SUMMARY OF THE INVENTION

The process of this invention overcomes the problems of the prior art by being extremely selective in hydrogenating the alkenyl substituent without hydrogenating the aromatic ring. In most cases there is no hydrogenation of the aromatic ring at all. Additionally, it has been found that no degradation or poisoning of the catalyst occurs when using hydrogen gas streams containing up to 30 per cent by volume carbon monoxide. Furthermore, the catalyst system of this invention is relatively inexpensive, does not require the expensive regeneration procedures of some of the commercial processes on the market today and has a relatively long catalyst life.

This invention provides a process whereby alkylbenzene is produced by hydrogenating alkylstyrene in the presence of a copper chromite catalyst. The alkylstyrene is preferably $\alpha$-methylstyrene and/or ring alkyl substituted $\alpha$-methylstyrene.

DESCRIPTION OF THE PREFERRED EMBODIMENT(S)

The term alkylstyrene refers to a compound wherein an alkyl group is substituted for at least one of the hydrogens on the styrene molecule. The alkyl substituents are preferably 1 to 8 carbon atoms in length. Ethyl and methyl substituents are preferred. As mentioned above, the preferred alkylstyrene is $\alpha$-methylstyrene and/or ring alkyl substituted $\alpha$-methylstyrene. The alkylbenzene produced obviously corresponds to the alkylstyrene used as a starting material.

The copper chromite catalyst useful in this invention is not limited to any particular form of copper chromite or to any particular copper chromite produced by a particular process. The copper chromite can be any of the catalytic copper chromites useful and/or known for hydrogenating various compounds. Copper chromite is usually designated $XCuO.Cr_2O_3$ wherein X has a value of from 0.5 to 2.5 See for example U.S. Pat. No. 3,767,595 which teaches an approved method of producing copper chromite catalyst. This reference is incorporated herein by reference.

The process is preferably carried out at a temperature of between about 100° C and about 250° C and at a pressure of between about 5 psia and about 300 psia. The conversion of alkylstyrene to alkylbenzene increases with increasing temperature and/or pressure and the effects of the two variables are related in such a way that 100 per cent conversion can be obtained in the case of $\alpha$-methylstyrene at a temperature as low as 100° C at a pressure of 300 psig, or as low as about 155° C at a pressure of 100 psig. It was also found that by operating at higher temperatures, it was possible to have the feed stream in a vapor and/or gaseous phase and thereby increase the amount of product produced per unit of catalyst used.

The hydrogen to alkylstyrene molar ratio is between about 1.3 and about 5.0 preferably. For $\alpha$-methylstyrene, the molar ratio of about 4.0 was found to be preferable when processing 72.9 and 66.7 per cent $\alpha$-methylstyrene feeds.

The hydrogen can be contacted with the $\alpha$-methylstyrene in any of the art-recognized manners. For example, flowing gas can be recycled to maintain the minimum cocurrent gas flow. Alternatively, the contacting can be enhanced by other means such as by switching to a counter-current reactor or installing an agitator. The downflow cocurrent trickle reactor is a preferred design for processes of the type involved.

The invention is further illustrated, but is not limited, by the following examples.

EXAMPLE 1

A batch hydrogenation system was assembled consisting of a 1-liter Parr autoclave equipped with gas inlet and outlet tubes, a liquid sampling tube, pressure gage, thermowell, stirrer, and electric heating jacket. To the autoclave was charged 200 grams of an oil containing 10 weight per cent $\alpha$-methylstyrene and 90 percent cumene, corresponding to a by-product stream from a cumene-phenol synthesis plant. Approximately 4 grams of a powdered commercial copper chromite catalyst (Harshaw Cu-1106: 39% CuO, 43.5% $Cr_2O_3$, 10% BaO) was mixed with the oil; the autoclave was then sealed, purged sequentially with nitrogen and hydrogen gas, then pressurized to 30 psig with hydrogen gas. The unit was heated, with stirring, to 145-150 C and 50 psig, at which point hydrogen uptake began. As the reaction proceeded, make-up hydrogen was added to maintain the pressure at 50 psig. At the end of 15 minutes, hydrogen absorption ceased, and the reactor was cooled. The oil product was separated from the spent catalyst and analyzed by vapor-phase chromatography. It was found to contain essentially 100 per cent cumene, indicating quantitative conversion of the AMS to cumene and no hydrogen attack on the aromatic nucleus.

EXAMPLE 2

The apparatus employed in Example 1 was used for this test. The charge to the reactor 200 grams of a cymene-dimethylstyrene (DMS) stream from synthesis of mixed cresols from meta- and paracymene. Prior to hydrogenation, the oil was caustic-washed to remove most of the phenolic contaminants. Four grams of copper chromite catalyst (Cu-1106) was mixed with the oil, and the hydrogenation sequence of Example 1 was repeated. The temperature was maintained at between about 150 and about 165 C for a total reaction time of about 60 minutes. The oil product, after separation from spent catalyst, was analyzed by vapor-phase chromatography. Results are listed in the accompanying table which gives the composition of (1) the original crude cymene-DMS stream (2) the same stream after caustic-washing to remove phenolics, and (3) the product oil from the hydrogenation reaction. Again, the styrene was quantitatively converted to alkylbenzene (m,p-cymene), and there was no hydrogen attack on the aromatic nucleus.

| Component, wt% | Crude Cymene-DMS Fraction | Fraction After Caustic-Washing | Hydrogenated Product |
|---|---|---|---|
| Acetone | 0.1 | 0.1 | 0.1 |
| m/p-Cymene | {87.3 | 85.9 | 96.4 |
| o-Cymene | | 3.1 | 3.5 |
| DMS | 10.6 | 10.9 | 0.0 |
| Phenolics | 2.0 | 0.06 | 0.0 |
| Other Components | — | 0.1 | — |

EXAMPLE 3

A continuous hydrogenation apparatus is operated at atmospheric pressure. The unit consists of a jacketed reaction vessel (1.6-cm ID); a microbellows pump for liquid feed, a gas cylinder; a pressure regulator, needle valve, and rotameter for gas-flow control; and a constant-temperature bath with external circulating pump to maintain temperature in the reactor jacket. A spiral coil of metal tubing at the bottom of the reactor served as an air-cooled condenser for the effluent, which was collected in a flask. From the bottom to the top of the hydrogenation reactor, the packing consisted of a support of 10 ml of glass beads, 90 ml of Harshaw Cu-1107 extruded copper chromite catalyst (33% CuO, 38% $Cr_2O_3$, 9.5% BaO, trace of $Na_2SiO_3$), and 30 ml of glass beads that served as a feed preheater. In operation, the reactor was brought to temperature by circulating heat-transfer oil from the constant-temperature bath, maintained at 173 C. The pump rate of the microbellows pump was adjusted to deliver 90 ml/hr of liquid feed, consisting of 11 per cent α-methylstyrene and 89 per cent cumene; the gas flow rate of pure hydrogen was adjusted to 300 ml/min (STP). Gas and liquid feed were passed co-currently downward through the reactor, and the product mixture was collected and analyzed. The unit was operated for 2 hours at the above conditions, to obtain steady-state operation, then a first sample was taken. After 6 additional hours of operation, a second sample was taken. Vapor-phase chromatographic analysis showed both samples to consist of essentially pure cumene; there was no detectable AMS in either sample, and no evidence of any cyclohexane derivatives, which would have been indicative of ring hydrogenation.

EXAMPLE 4

The same apparatus, with the same catalyst packing are used in Example 3, was used in this test. In this test, the hydrogenation gas was a mixed gas containing 30 per cent CO-70 per cent $H_2$. The liquid feed rate was maintained at 90 ml/hr (of 11% α-methylstyrene, 89% cumene); gas flow rate for the mixed gas was 370 ml/min (STP), and the temperature of the circulating heat-transfer oil from the constant-temperature bath was 173 C. After 2 hours of operation, a first sample was taken, and after 6 additional hours, a second sample was taken. Analysis (by vapor-phase chromatography) showed both samples to be essentially pure cumene; there was no detectable AMS and no evidence of ring hydrogenation.

It is true, of course, that noble-metal catalysts such as Pt or Pd are active in promoting this type of hydrogenation reaction. Indeed, a test was made in whih 11 per cent AMS - 89 per cent cumene was hydrogenated in the Parr unit at a temperature of about 72 C, pressure of about 20 psig, for a reaction time of 30 minutes. Analysis of the product oil indicated complete conversion of the contained α-methylstyrene to cumene. However, noble-metal catalysts are readily poisoned and deactivated by CO that would be present in a synthesis or waste gas, such as was employed in Example 4. Only the rugged and CO-resistant chromite catalysts would be effective for use with this type of hydrogenating gas.

Analytical data reported in the above Examples 1-4 were re-examined for the purpose of establishing reliability with respect to detection and measurement of styrenes in the feed to the hydrogenation process, and residual styrenes and cyclohexane derivatives in the hydrogenation product. Cyclohexanes would result from hydrogenative attack on the aromatic nucleus, as indicated below:

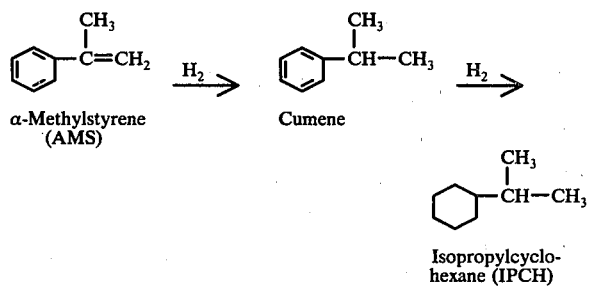

Analysis of all samples of the product of Examples 1-4 was by means of a gas-chromatographic technique. An F & M Model 810 Chromatograph was employed, containing a 12 feet × ¼ inch column packed with 10 percent Paraplex U-148 on support of 60–80 mesh Gas Chrom-P. Oven temperature of the gas-chromatograph was programmed from 100° C to 180° C at the rate of 2° per minute and was then maintained isothermal to the end of the determination. Gas chromatograph injection port temperature was 300° C, and detector temperature was 200° C; detection was by the flame-ionization technique. The carrier gas was helium employed at a flow rate of about 80 milliliters per minute.

Inspection of the chromatograms indicated virtually complete conversion of the styrene derivative; that is, the residual concentration was significantly less than 200 ppm (<0.02%)—the limit of detectability of the equipment. Furthermore, the presence of cyclohexane derivative was also shown to be significantly less than the 200 ppm level in the product oil; the concentration could possibly even be zero. As an industrial chemical, the cumene would be regarded as being chemically "pure" or essentially devoid of impurities.

To carry this further, industrial-grade cumene that is currently employed for the manufacture of phenol has the following typical analysis:

| Component | Percent |
|---|---|
| Cumene | 99.94 |
| Benzene | <0.01 |
| n-Propylbenzene | 0.02 |
| t-Butylbenzene | 0.01 |
| α-Methylstyrene | 0.01 |
| Miscellaneous Components | Ca. 0.02 |

This is regarded as a high-purity cumene feedstock for conversion to phenol via hydroperoxidation. Thus, the ultra-low concentrations of AMS found in the hydrogenated AMS products of this invention would have no effect at all on the rated purity of recycle cumene fraction. The same rationale applies to hydrogenation of dimethylstyrenes, such as are produced as by-products during conversion of m,p-cymene to m,p-cresol via the same processing sequence.

The results obtained herein are in marked contrast to Neta et al U.S. Pat. No. 3,769,358 in which claims of resistance to nuclear hydrogenation are accompanied by analytical data in Table 2 of Neta et al that show significiant concentration of IPCH in the products resulting from hydrogenation of AMS—on the range of several tenths of a percent up to almost two percent.

Substantially complete suppression of formation of IPCH as shown in the invention of this application is of considerable importance in the cumene hydroperoxidation process. IPCH has a reported normal boiling point of 154.5° C, while cumene has a boiling point of 152–3° C (Handbook of Chemistry and Physics, 45th ed.). It would, therefore, be extremely difficult to separate IPCH from cumene by ordinary distillation techniques; costly superfractionation would be required. Failing this and assuming inertness of IPCH in the hydroperoxidation reaction, the concentration of IPCH would increase upon recycle of cumene regenerated by hydrogenation of AMS. This would necessitate a continuous purging of recycled product to maintain IPCH concentration within tolerable limits. Purging, of course, entails a loss of cumene and imposes an economic penalty on the over-all process.

If, on the other hand, IPCH is at all susceptible to cooxidation with cumene, it could produce a series of contaminating impurities in the phenol product (alcohol, ketone) which would be difficultly separable and could render the phenol useless for certain applications.

It is, therefore, of crucial importance that the IPCH be substantially completely prevented from forming during the process of hydrogenating AMS. This objective is achieved in the invention of this application.

We claim:

1. In the process for producing alkylbenzene by hydrogenating a feed stream comprising α-alkylstyrene, the improvement comprising carrying out the hydrogenation in the presence of a copper chromite catalyst.

2. Process as in claim 1 wherein said feed stream comprises α-methylstyrene or benzene ring alkyl substituted α-methylstyrene or mixtures thereof.

3. Process as in claim 2 wherein the feed stream also contains cumene.

4. Process as in claim 2 wherein the hydrogenation is carried out at a temperature of between about 100° C and about 250° C and at a pressure of between about 5 psia and about 300 psia.

5. Process as in claim 4 wherein the hydrogenation is carried out using a hydrogen stream containing carbon monoxide in amounts of up to about 30% by volume.

6. Process as in claim 5 wherein the hydrogen is present in an amount such that the hydrogen to α-methylstyrene or benzene ring alkyl substituted α-methylstyrene or mixtures thereof molar ratio is between about 1.3 and about 5.0.

7. In a process for producing alkylbenzene by hydrogenating a reaction mixture resulting from the production of phenol by oxidation of cumene and decomposition and dehydration of the reaction product, which reaction mixture comprises (1) cumene and (2) α-methylstyrene or benzene ring alkyl substituted α-methylstyrene or mixtures thereof, the improvement comprising carrying the hydrogenation out in the presence of a copper chromite catalyst.

8. Process as in claim 7 wherein the α-methylstyrene or benzene ring alkyl substituted α-methylstyrene or mixtures thereof is present in an amount between about 10 and about 80% by weight.

9. Process as in claim 8 wherein the hydrogenation is carried out at a temperature of between about 100° C and about 250° C and at a pressure of between about 5 psia and about 300 psia.

10. Process as in claim 9 wherein the hydrogenation is carried out using a hydrogen stream containing carbon monoxide in amounts of up to about 30% by volume.

11. Process as in claim 10 wherein the hydrogen is present in an amount such that the hydrogen to α-methylstyrene or benzene ring alkyl substituted α-methylstyrene or mixtures thereof molar ratio is between about 1.3 and 5.0.

12. In the process for producing alkylbenzene by hydrogenating a crude feed stream comprising cumene and α-methylstyrene, the improvement comprising carring out the hydrogenation in the presence of the copper chromite catalyst and wherein the α-methylstyrene is present in an amount between about 10 and about 80% by weight and wherein the hydrogenation is carried out at a pressure of between about 5 psia and about 300 psia and wherein the hydrogen stream contains carbon monoxide in amounts of up to about 30% by volume.

13. Process as in claim 12 wherein the hydrogen is present in an amount such that the hydrogen to α-methylstyrene molar ratio is between about 1.3 and 5.0.

14. Process as in claim 13 wherein the temperature is maintained sufficiently high to maintain the feed stream as a gas or vapor or mixtures thereof.

* * * * *